United States Patent [19]

Metcalfe

[11] Patent Number: 4,952,151
[45] Date of Patent: Aug. 28, 1990

[54] METHOD AND APPARATUS FOR PREPARING REPLACEMENT DENTAL STRUCTURES

[76] Inventor: Edwin R. Metcalfe, 503 Armstrong, Apartment 1, Kansas City, Kans. 66101

[21] Appl. No.: 240,713

[22] Filed: Sep. 6, 1988

[51] Int. Cl.$^5$ .............................................. A61C 5/10
[52] U.S. Cl. .................................... 433/223; 433/53; 433/74; 433/213; 433/214
[58] Field of Search ...................... 433/49, 53, 63, 65, 433/72, 74, 213, 214, 218, 222.1, 223

[56] References Cited

U.S. PATENT DOCUMENTS

| | | | |
|---|---|---|---|
| 1,675,732 | 7/1928 | Schweitzer | 433/218 |
| 1,950,865 | 3/1934 | Stansbury | 433/72 |
| 3,375,582 | 4/1968 | Myerson | 433/223 |
| 3,417,471 | 12/1968 | Mitchell | 433/72 |
| 4,017,972 | 4/1977 | Glenn | 433/74 |
| 4,521,187 | 6/1985 | Casper | 433/72 |

*Primary Examiner*—John J. Wilson
*Attorney, Agent, or Firm*—Kokjer, Kircher, Bradley, Wharton, Bowman & Johnson

[57] ABSTRACT

An apparatus for use in preparing both metal and porcelain dental crowns. The apparatus has a plurality of upright supports and arms coupled therewith that are moved to contact with the tooth opposing the tooth to be crowned in the proper occlusal locations such that when the permanent crown is prepared it has all of the proper occlusal characteristics of the opposing dental structure. The apparatus is intended for use in and with a replica of the patient's dental structures. The apparatus has a plurality of pathways upon which the upright supports may be moved so as to position the supports in the proper contact points. Methods for utilizing the apparatus when preparing metal and porcelain crowns are also provided. A preformed, imitation dental crown having four layers for use in preparing porcelain crowns where each layer corresponds to one of the layers of porcelain or metal necessary to prepare the finished porcelain crown is also provided.

23 Claims, 2 Drawing Sheets

U.S. Patent   Aug. 28, 1990   Sheet 1 of 2   4,952,151
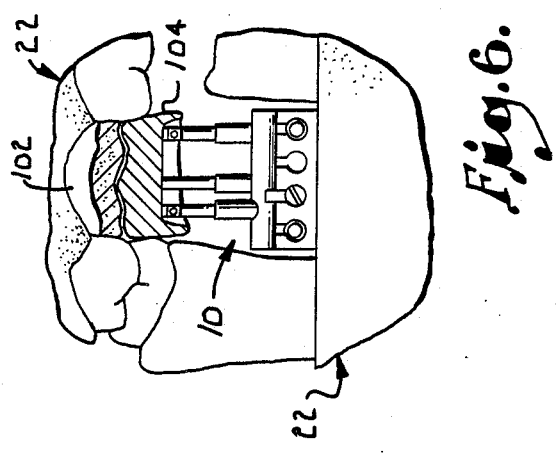
Fig. 5.
Fig. 6.
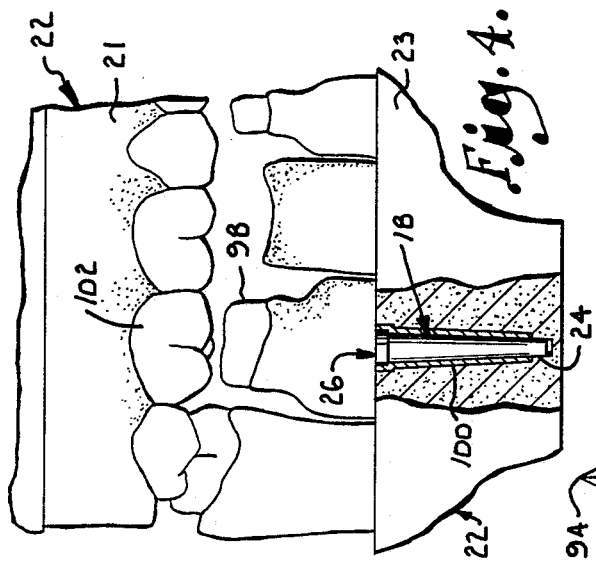
Fig. 4.
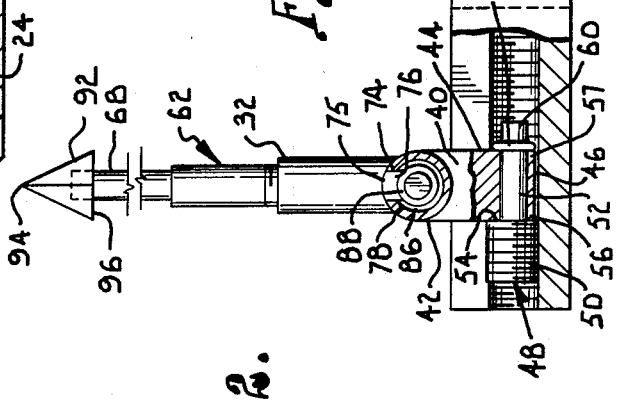
Fig. 3.
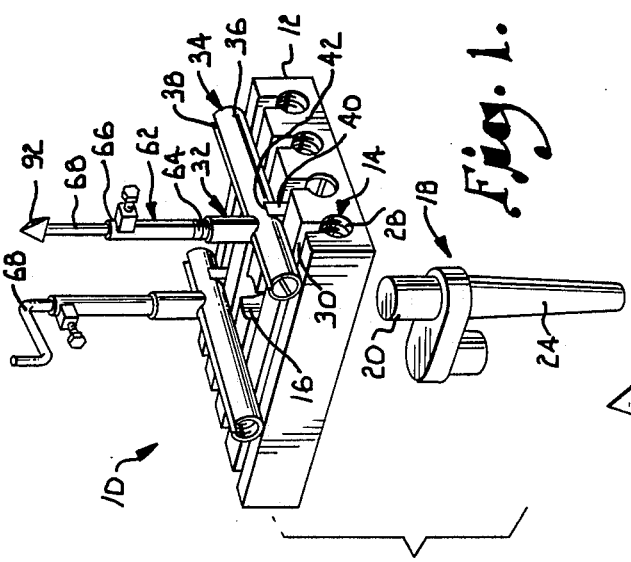
Fig. 1.
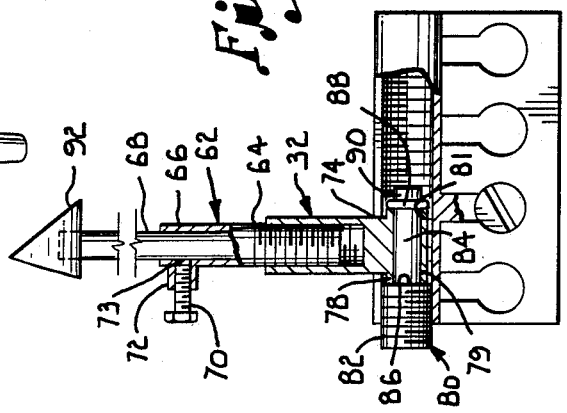
Fig. 2.

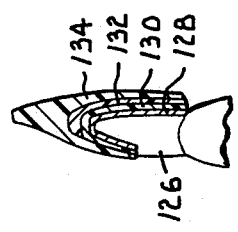
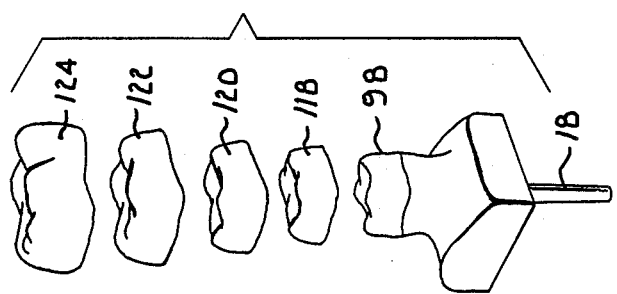
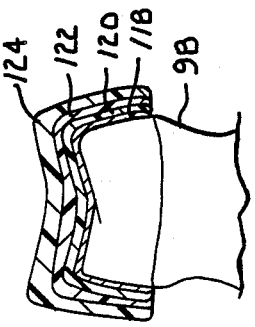
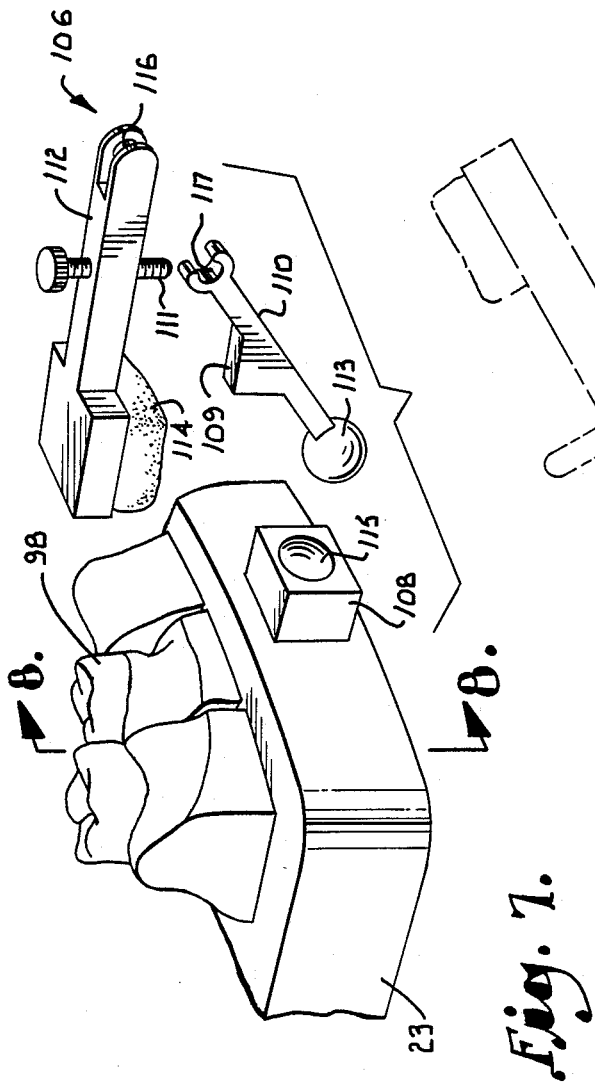
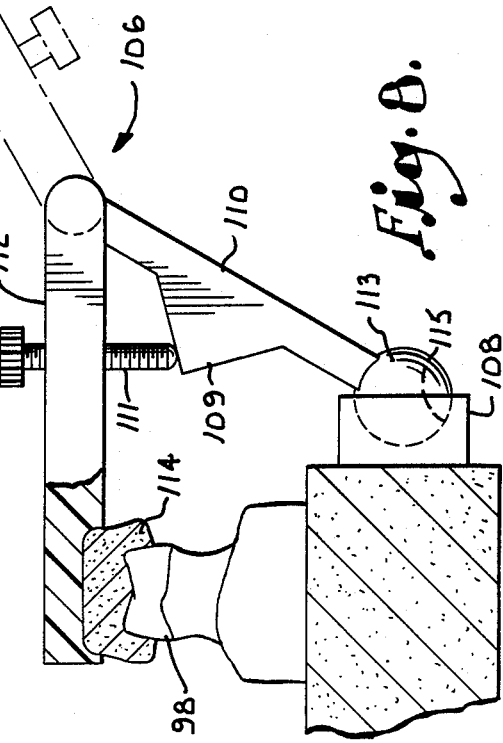

METHOD AND APPARATUS FOR PREPARING REPLACEMENT DENTAL STRUCTURES

BACKGROUND OF THE INVENTION

This invention relates in general to the field of dentistry and, more particularly, to an apparatus for use in preparing crowns for posterior teeth. Moreover, this invention relates to methods for preparing dental crowns and for preparing replacement dental structures.

An important aspect of an individual's overall physical health is good oral hygiene. When a tooth becomes damaged or diseased it is imperative that the problem be remedied. Damaged or diseased teeth, such as molars, bicuspids and anterior teeth, are often repaired by the addition of a dental crown to the affected tooth. Sometimes the tooth must be removed completely and replaced by an imitation dental structure.

As can be appreciated, great care must be taken when preparing dental crowns or replacement teeth. The replacement dental work must conform to the opposing dental structures so as to not alter the occlusal characteristics, or bite, of a patient's teeth. The replacement dental work must also be capable of being done in a timely manner.

The first step in preparing replacement dental work is for the dentist to prepare the damaged or diseased tooth. For a posterior tooth, this normally consists of grinding the tooth to a base structure. For an anterior tooth, this either requires extraction of the tooth or grinding the tooth to a base structure. The dentist then takes an impression of the patient's entire dental structure, both top and bottom sets of teeth. From these impressions, a model of the patient's dental structures is prepared. This model is often referred to as fractory work. This model is a replica of the patient's set of teeth and the top and bottom sets of teeth are coupled together by a hinge or the like in a manner corresponding to the patient's occlusal characteristics. The model is cut up or sectioned into as many pieces as necessary so that the technician preparing the dental work can work easily with the individual replica of the tooth needing repair.

Currently, the most widely utilized method for preparing a metal crown for a posterior tooth starts by removing the replica of the tooth to be crowned from the model and dipping the tooth in a wax or other similar substance to form a thin coat around the tooth. The replica tooth is often referred to as being "waxed-up" at this point. The tooth has previously been coated with a lubricant so that the wax impression may be removed from the replica. Additional wax is then transferred to the "waxed-up" replica to build a wax crown that corresponds to the occlusal characteristics of the tooth's opposing dental structure. Obtaining the correct occlusal and anatomical characteristics on this wax tooth is done by the technician visually attempting to copy the correct characteristics, especially the custip or contact points of one tooth with its opposing teeth, on a trial and error basis whereby wax is added or cut away until the technician believes a properly formed tooth is prepared. As can be seen, this requires a great deal of knowledge of proper dental anatomy and an artist's skill in transferring the characteristics of the opposing dental structure or structures to the wax crown being prepared. Once a satisfactory wax crown is obtained, the wax crown is removed from the replica of the tooth and converted into a metal crown for permanent placement on the patient's tooth.

If a porcelain crown is to be prepared, essentially the same method is utilized except that only a thin layer of metal is first prepared from the "waxed-up" replica as the underlying base structure of the crown. Porcelain material is then added onto this metal base structure again until the technician believes that the proper occlusal and anatomical characteristics of the damaged tooth to its opposing dental structures is formed. Again, this requires a great deal of time and skill to prepare a proper and accurate porcelain crown.

Replacement anterior teeth are typically prepared by a similar trial and error method where the porcelain is added to a base metal structure by the technician until it is believed that the proper occlusal and anatomical characteristics of the tooth have been obtained.

As can be seen, the methods currently employed in preparing replacement dental work are time consuming in that a trail and error method is utilized. Additionally, no uniformity or consistency from one crown to the next is possible since each individual crown or replacement dental structure is dependent upon the skill of the technician preparing that particular replacement dental structure. The importance of having the replacement dental work correspond accurately to its opposing dental structures is paramount in maintaining the integrity of the patient's occlusal characteristics and much accuracy is lost when the preparation of the crown or other dental work relies upon the skill of the technician in visually copying the anatomical characteristics of the dental structures involved.

It is therefore a primary object of the present invention to provide an apparatus for use in preparing dental crowns that enables crowns to be made quickly and accurately that correspond to the the proper occlusal and anatomical characteristics of the patient's dental structures without relying upon the individual artistic skill of the technician involved.

It is a further object of the present invention to provide such an apparatus that can be positioned so that the proper custip or contact points of the tooth to be crowned with its opposing dental structures can be integrated into the crown without the need for guesswork or artistic ability on the part of the technician.

It is another object of the present invention to provide an apparatus for use in preparing dental crowns that has a plurality of pathways and a plurality of upright supports that enable the custip points of the opposing dental structure to be properly positioned on the crown being prepared.

It is still another object of the present invention to provide such an apparatus having caps on the top of the upright supports so as to pinpoint the location of the custip points on the crown being prepared.

It is an aim of the present invention to provide a method for preparing metal or porcelain crowns utilizing the apparatus of the present invention that produces anatomically accurate dental crowns without relying on a technician's skill or ability.

It is still another aim of the present invention to provide a preformed wax crown comprising at least four individual, separate layers that correspond to the layers of porcelain and metal utilized when preparing replacement porcelain dental structures.

It is still another aim of the present invention to provide such preformed, four-layered, wax crowns in a variety of sizes to accommodate most normally sized dental structures.

It is yet another aim of the present invention to provide a preformed, four-layered, wax crown that is adapted for use in preparing porcelain crowns or replacement porcelain dental structures for anterior teeth.

It is an additional aim of the present invention to provide methods for preparing dental crowns for anterior or posterior teeth utilizing the preformed, four-layered, wax crowns in a manner that produces anatomically correct crowns or replacement dental structures quickly and accurately without relying on the individual artistic skill of the technician.

It is a still further aim of the present invention to provide a method and apparatus that can be utilized advantageously for preparing a full mouth restoration, such as bridges to replace dentures, that reduces the time and labor currently required in preparing such dental work.

It is also an aim of the present invention to provide apparatus and methods that are particularly adaptable to use with dental implants.

Other and further objects of the present invention will become apparent from the following description of the invention and the accompanying drawings.

SUMMARY OF THE INVENTION

I have discovered that an apparatus having a plurality of linear pathways to which upright supports are coupled thereto can be used advantageously in preparing dental crowns. Use of this apparatus allows for the custip points of the crown to be quickly located and accurately reproduced in the permanent crown. The height of the upright supports can be varied and the supports can be moved in two different directions on the apparatus so as to enable the supports to be positioned at the correct custip locations. Further, the custip points can be pinpointed by use of caps on arms extending from the upright supports. This apparatus may be used to prepare both metal and porcelain crowns.

I have further discovered that a four-part, preformed, imitation crown can be used advantageously to quickly and accurately prepare a porcelain crown. The four-part, preformed, imitation crown comprises wax replicas of each of the layers of porcelain and metal necessary to make a porcelain crown. This four-part, preformed, imitation crown comprises a coping layer, a body layer, an incisal layer and an overbuild layer. These crowns are prepared in a variety of sizes and such crowns are made for both anterior and posterior teeth. These four-part, preformed, wax crowns permit the technician to obtain an impression in modeling clay or the like of each successive layer as it is placed on the tooth to be crowned. These impressions are then used to mold each successive layer of porcelain used when preparing porcelain crowns thereby providing a method to quickly and accurately form a properly shaped porcelain crown.

BRIEF DESCRIPTION OF THE DRAWINGS

In the accompanying drawings in which like reference numerals are used to indicate like parts in the various views:

FIG. 1 is a perspective view of the apparatus of the present invention;

FIG. 2 is a fragmentary front elevational view of the apparatus of the present invention partially cut away;

FIG. 3 is a fragmentary side elevational view of the dental apparatus of the present invention;

FIG. 4 is a side elevational view of a model of a patient's dental structures;

FIG. 5 is a side elevational view illustrating the use of the dental apparatus with a model of a patient's dental structures;

FIG. 6 is a side elevational view illustrating use of the dental apparatus with a model of a patient's dental structures in conjunction with a preformed wax crown pursuant to one of the methods of the present invention.

FIG. 7 is a perspective view of a hinged articulator used in a method of the present invention.

FIG. 8 is a side sectional view of FIG. 7 showing the hinged articulator as used in one of the methods of the invention.

FIG. 9 is an exploded, perspective view of the four-part, preformed, imitation crown feature of the present invention.

FIG. 10 is a side sectional view of the four-part, preformed, imitation crown as used in a method of the present invention.

FIG. 11 is a side sectional view of another embodiment of a four-part, preformed wax crown adapted for use with anterior teeth.

DESCRIPTION OF THE PREFERRED EMBODIMENT

Referring initially to FIG. 1, the apparatus of the present invention is designated generally by the numeral 10 and has a base 12. The base presents a plurality of first linear pathways 14 extending transversely of base 12. Four pathways 14 are so defined in FIG. 1. An opening 16 is presented through base 12 to receive pin 18. Top section 20 of pin 18 is adapted to be received in opening 16. When pin 18 is coupled to base 12, apparatus 10 may be removably coupled with model 22 by insertion of lower portion 24 of pin 18 into an appropriately sized opening 26 in model 22. Model 22 is a replica of the patient's set of teeth or dental structures. The tooth needing repair is made to be removable from model 22. Another pin 18 is permanently placed in the bottom of the replica of the tooth as seen in FIG. 4. Opening 26 in model 22 is prepared to receive pins 18 and is often prepared with a thin metal plate 100 for support.

Each of pathways 14 have a lower section 28 that is generally circular and an upper slot 30. The lower section 28 of a pathway 14 is threaded longitudinally of the pathway and slot 30 is in communication with lower section 28. This construction of pathway 14 allows for coupling of either an upright support 32 with a pathway 14 or means for defining a second linear pathway 34 with pathway 14.

As shown in FIG. 1, a second linear pathway 34 is coupled with one of the first linear pathways 14. Second linear pathway 34 is preferably defined by a tube 36 having a longitudinally extending slot 38 in communication with tube 36. Tube 36 is threaded longitudinally of pathway 34.

Referring to FIG. 3, the means for coupling a second linear pathway 34 with a first linear pathway 14 is further illustrated. A coupling member 40 is secured to tube 36 by welding or gluing or the like. Coupling member 40 has a top end 42 that is concave to receive tube 36 and to hold same in a cradle-like fashion. The bottom end 44 of coupling member 40 extends through slot 30 and into lower section 28 of pathway 14. A hollow tube 46 is coupled with the bottom end 44 of coupling member 40 by welding, gluing or other like manner of securement. Bottom end 44 may be convexly shaped to receive tube 46 or may, alternatively, be flat bottomed and have tube 46 attached thereto. Coupling member 40 may, preferably, have tube 46 formed integral therewith.

Tube 46 is dimensioned so as to be received within lower section 28 of a first linear pathway 14. This allows for tube 46 and coupling member 40 to move along first linear pathway 14 and thereby moving the second linear pathway 34 coupled thereto. The means for controlling the movement of the second linear pathway 14 is best shown in FIG. 3.

A screw 48 having a first threaded section 50 and a second unthreaded section 52 is inserted into the first linear pathway 14 in order to provide for movement of the second linear pathway 34 coupled therewith. Unthreaded section 52 is dimensioned to be received in hollow tube 46 and to extend therethrough. Threaded section 50 is dimensioned to be threadably received in first linear pathway 14. Thus, screw 48 has two widths whereby the threaded section 50 is wider than the unthreaded section 52. Threaded section 50 of screw 48 has a distal end 54. When screw 48 is inserted through tube 46, the distal end 54 of threaded section 50 of screw 48 contacts with one end 56 of tube 46. When screw 48 is further threaded into first linear pathway 14, distal end 54 pushes tube 46 and thereby its correspondingly coupled second linear pathway 34 along first linear pathway 14. The end 54 of screw 48 pushes against the end 56 of tube 46 thereby causing the coupling member 40 to move within first linear pathway 14. A second linear pathway 34 may thereby be positioned at any location desired along a first linear pathway 14.

In order to reverse the movement of a second linear pathway 34 along a first linear pathway 14, a means for maintaining the screw 48 in relationship with tube 46 is presented on screw 48. 0-ring 58 is coupled to screw 48 near the distal end 60 of unthreaded section 52. 0-ring 58 fits around unthreaded section 52 in a manner such that when screw 48 is threaded in the reverse direction as discussed above, 0-ring 58 contacts with the opposite end 57 of tube 46 thereby pulling tube 46 and the second linear pathway 34 coupled thereto in the opposite direction along first linear pathway 14. As can be seen, this overall arrangement accommodates rectilinear movement of the second linear pathway 34 along first linear pathway 14.

As illustrated in FIG. 1, upright support 32 is coupled with a second linear pathway 34. At least one upright support 32 is coupled with each second linear pathway 34. Upright support 32 may be coupled directly with first linear pathway 14. Direct coupling of upright support 32 with first linear pathway 14 would accommodate rectilinear movement of upright support 32 along first linear pathway 14. In order to accommodate transverse movement of upright support 32 in relation to first linear pathway 14, upright support 32 is coupled to second linear pathway 34 in a manner to accommodate such movement.

Referring now to FIGS. 1-3, upright support 32 is tubular and is threaded along its inner surface. An arm 62 having a lower section 64 threaded about its outer surface and an upper unthreaded section 66 is threadably received in upright support 32. Arm 62 is also tubular and adapted to receive an extension arm 68 therein. Arm 62 is equipped with means for holding extension arm 68 at a desired position above arm 62. The preferred means includes a tubular extension 72 extending generally perpendicular from arm 62 and being threaded about its inner surface. Tubular extension 72 is in communication with the inner portion of tubular arm 62. A set screw 70 is threadably received in extension 72 so that the distal end 73 of screw 70 contacts with extension arm 68 and holds it securely within tubular arm 62.

Upright support 32 is coupled to second linear pathway 34 by means similar to that coupling second linear pathway 34 with first linear pathway 14. As best shown in FIG. 3, a coupling member 74 is attached at its upper end 75 to the bottom of arm 32 and extends through slot 38 of second linear pathway 34. A lower end 76 of coupling member 74 is coupled to a hollow tube 78 which is dimensioned to be received within tube 36 defining the second linear pathway 34.

In order to facilitate rectilinear movement of upright support 32 along second linear pathway 34 transverse to first linear pathway 14, a screw 80 having a threaded section 82 and an unthreaded section 84 is threadably received in tube 36. Unthreaded section 84 is of a width less than that of threaded section 82 and is received within tube 78. The distal end 86 of threaded section 82 of screw 80 contacts with one end 79 of tube 78 such that when screw 80 is threaded into tube 36, tube 78, and the upright support 32 coupled therewith are pushed along second linear pathway 34. To reverse the direction of movement of upright support 32 along second linear pathway 34, 0-ring 88 is coupled near the distal end 80 of unthreaded section 84 of screw 80. When screw 80 is threaded in a reverse direction relative to that described above, 0-ring 88 contacts with the opposite end 81 of tube 78 and pulls tube 78 and its correspondingly coupled upright support 32 in the opposite direction along second linear pathway 34.

Extension arm 68 may be straight or may be bent, as shown in FIG. 1, to facilitate proper alignment of arm 68 when the apparatus 10 is used for preparing dental crowns. Cap means 92 are also provided to be positioned atop extension arm 68. Cap 92 is generally pyramid shaped and has a rounded point 94 at its top. The base 96 of cap 92 has a notch therein to accommodate the upper end of extension arm 68 so that cap 92 fits securely on arm 68.

When apparatus 10 is formed as described above, an upright support 32 can be be moved to any desired position along first linear pathway 14 and can also be moved to any desired position along second linear pathway 34. Through the use of arm 62 and extension arm 68, the height of upright support 32 may be varied to any height desired for use. Thus, the upright support 32 and its attached arms or extension arms may be positioned at any location on base 12. Through the use of a bent extension arm, the position of extension arm 68 and cap 92 may further be moved to any location above base 12 by rotating the bent extension arm 68 in relation to arm 66.

In the preferred embodiment of the present invention, base 12 has four first linear pathways 14 extending transversely of base 12. Extending transversely of first linear pathways 14 and coupled therewith are four second linear pathways 34. Coupled with each second linear pathway is an upright support 32 having a first arm 62 and an extension arm 68 coupled thereto to provide vertical movement of arms 62 and 68 relative to upright support 32. The free end of extension arms 68 are equipped with a cap 92.

The apparatus 10 may be made of any suitable material, but is preferably formed out of a lightweight metal such as aluminum or steel. The apparatus 10 can be dimensioned in various sizes so that it can be adapted to fit into a variety of differently sized models 22 of a patient's dental structures.

Apparatus 10 has primary utility for assisting in the preparation of dental crowns for a posterior tooth, such as a molar or bicuspid. In order to prepare the crown, the dentist must have first prepared the tooth to be crowned. An impression of the patient's dental structures is then taken by any method presently known in the dental art and a model of the patient's dental structures is prepared therefrom. This model, shown in FIGS. 4–6 and designated generally by the numeral 22, is often referred to as fractory work and is a replica of all of the dental structures of the patient. The upper plate 21 and lower plate 23 of the patient's dental structures are also arranged to accurately correspond with the occlusal or "bite" characteristics of the patient. This proper occlusal contact is maintained by connecting upper plate 21 and lower plate 23 together by a hinge or other means known in the dental art (not shown). This allows for one of the plates to be removed from contact with the other plate and returned again without altering any of the characteristics of the patient's bite characteristics. The dental structure or tooth to be crowned is further adapted to be removable from model 22.

Referring to FIG. 4, the replica of the dental structure needing a crown is designated by the numeral 98. This replica is removably coupled to model 22 by means of a pin 18 attached to the bottom of the tooth 98. An opening 26 is presented in the bottom plate 23 of model 22 to accommodate pin 18. The opening 26 may be lined with a thin metal plate 100 surrounding opening 26. In this manner, tooth 98 may be removed from model 22.

When forming a crown for a damaged tooth, the technician or person preparing the crown must know the anatomy of the tooth to be crowned. This can be ascertained with reference to its opposing dental structure or structures. A tooth contacts with its opposing dental structures at discrete points known as custip points. For molars, there are usually three or four custip points and for bicuspids there are typically two custip points. Knowing how many custip points to expect in the tooth to be crowned allows the technician to prepare apparatus 10 with the proper number of upright supports 32, arms 62 and extension arms 68 thereon.

To prepare a crown utilizing the apparatus 10 of the present invention, replica tooth 98 is removed from model 22 and apparatus 10 is placed in that position in model 22. The top plate 21 of model 22 is then closed onto and placed in occlusal contact with lower plate 23. As this is done, the dental structure or structures that normally contact with tooth 98 are positioned above apparatus 10. As shown in FIGS. 4–6, one dental structure, tooth 102, is shown as being in occlusal contact with tooth 98. Upright supports 32 and arms 62 and 68 coupled therewith are moved to the proper locations, the custip points, on the dental structure 102 opposing tooth 98. By moving supports 32 along either first linear pathway 14 or second linear pathway 34 or both, the exact points where tooth 98 should contact with its opposing dental structure 102 can be located and the upright supports 32 can be set at that point. Caps 92 assist in providing pinpoint placement of upright supports 32 into the proper custip points of opposing tooth 102. Creating the proper occlusal contact of apparatus 10 with the custip points of tooth 102 is further enhanced by the vertical movement of arms 62 or 68 on supports 32 or by the use of a bent extension arm 68.

Once the upright supports 32 and arms 62 or 68 of apparatus 10 are positioned in proper occlusal contact with opposing dental structure 102, top plate 21 is removed from contact with apparatus 10. The distances between the upright supports 32 of apparatus 10 are measured and the height of the extension arms 68 are also measured to determine the proper size one-piece, imitation wax crown 104 to be used. After the proper size of the one-piece, imitation crown is determined, the technician obtains a properly sized imitation crown 104 from an already existing set of such crowns. One-piece, imitation wax crowns of this nature are already known in the art of dentistry and come in a variety of sizes, shapes and depths to fit most any size dental structure needing to be crowned. The crown is typically made of wax, but may be made of any other moldable material that can later solidify to create a permanent impression.

Once the properly sized imitation crown 104 is selected, it is typically placed onto the arms 62 of apparatus 10 after extension arms 68, if used, have been removed. Extension arms 68 are removed to accommodate for the depth of crown 104. If a wax crown is being used, it must first be heated so that it is moldable. The opposing dental structure 104 is then closed down onto and placed into contact with the moldable, imitation, wax crown 104. As the opposing dental structure or tooth 102 contacts with the moldable crown 104, the appropriate custip points and other anatomical features of the crown are formed into imitation crown 104. Upright supports 32 and arms 62 assure that imitation crown 104 will contact with opposing tooth 102 at all of the correct custip points and that wax crown 104 will be molded with the proper occlusal characteristics of opposing tooth 102.

The now properly molded one-piece, imitation crown 104 is maintained in contact with opposing tooth 102 by use of an adhesive material to temporarily maintain contact of the crown 104 with the opposing tooth 102. The upper plate 21 is then opened so as to remove opposing tooth 102, with crown 104 adhered thereto, from contact with apparatus 10. Apparatus 10 is then removed from the model 22 so that tooth 98 may be placed back into model 22. Replica tooth 98 has previously been sprayed or lubricated with a lubricant and then dipped in wax forming a wax coating surrounding tooth 98. The lubricant allows this wax coating to be easily removed from tooth 98. This "waxed-up" tooth 98 is placed back into model 22 and the opposing dental structure 102 with molded imitation crown 104 coupled thereto is again placed in contact with "waxed-up" tooth 98. Another piece of adhesive material, such as a small piece of wax, is placed on the top of tooth 98 so that when imitation crown 104 is placed in contact with tooth 98, crown 104 will transfer from opposing tooth 102 to tooth 98. Once imitation crown 104 is transferred onto "waxed-up" tooth 98, opposing tooth 102 is again removed from contact with bottom plate 23.

At this point a one-piece, imitation crown having all of the correct anatomical features and custip points of the tooth to be crowned is positioned on top of tooth 98. Additional wax is now added to integrate imitation crown 104 with the waxed-up tooth 98 at the points of contact of imitation crown 104 with waxed-up tooth 98, this step is generally known as sealing the margins. The imitation crown 104 is now in condition to be made into a metal, permanent crown by methods known in the dental arts.

It is often desirable that the dental crown or other dental structure being formed be made of a porcelain material so that the replacement dental structure blends in with the patient's remaining teeth. The apparatus 10 of the present invention can advantageously be used to assist in preparing porcelain crowns for posterior teeth. When performing this method, apparatus 10 is again placed in model 22 at the position where the tooth to be crowned is located. The opposing dental structure 102 is closed down over apparatus 10 and arms 68 of apparatus 10 are moved into the proper contact positions with opposing dental structure 102. Next, opposing dental structure 102 is removed from contact with apparatus 10 and the spacer arms 68 are removed from the apparatus 10. The distances between the arms 62 are measured in order to determine the correct size of preformed, imitation dental structures to be utilized for preparing the porcelain crown.

At this point, another novel feature of the present invention is utilized in the preparation of a porcelain dental crown. When porcelain crowns are prepared, a plurality of layers of porcelain must be applied to a base structure to form the finished crown. Four layers of material are typically used in preparing a porcelain crown. The bottom layer which will be in direct contact with the remaining portion of the patient's tooth is called the coping and is normally prepared out of a thin layer of metal that has been coated with a very thin layer of a porcelain material called the opaque layer. The opaque layer coats the metal for easier binding of the following porcelain layers. The second layer is called the body layer and is prepared out of porcelain material and forms a thin layer of porcelain over the coping. The third layer is called the incisal layer and is again formed out of porcelain material or the like to conform to the necessary anatomy of the opposing dental structure. The fourth layer is called the overbuild layer and is again prepared out of porcelain. The purpose of the overbuild layer is to provide ample porcelain on the crown being prepared so that when the porcelain crown is baked, it will shrink to the appropriate size. It is common for porcelain to shrink somewhat during the baking stage.

Referring now to FIGS. 9 and 10, a preformed, imitation dental crown having four layers, these layers corresponding to each of the three layers of porcelain required to prepare a porcelain dental crown and one layer corresponding to the coping layer are prepared in a variety of sizes to accommodate most sizes of posterior teeth. These preformed, imitation dental structures are preferably made out of wax. Therefore, if a porcelain crown is to be prepared for tooth 98, which is shown individually in FIG. 9, a wax coping layer 118, a wax body layer 120, a wax incisal layer 127, and a wax overbuild layer 124 are obtained in the appropriate size to correspond to the various depths of porcelain required for each stage of preparing a porcelain dental crown. Each of these preformed layers are generally rectangular in shape for use on posterior teeth. Each layer has an upper surface and sides extending downward from the upper surface. The upper surface is of a thickness or depth corresponding to the depth of porcelain needed to make that particular layer of the porcelain crown. The combined depth of the four layers when positioned together, as shown in FIG. 10, approximates the depth of the finished porcelain crown when the shrinkage of the porcelain is taken into account. The upper surface may be smooth or may have some general occlusal characteristics preformed therein.

Once the proper size of the preformed, imitation dental crown to be used for the particular tooth being crowned is determined by use of apparatus 10, each of these layers are placed onto apparatus 10. The coping layer 118 is placed directly onto arm 62 of apparatus 10, body layer 120 is placed atop coping 118, incisal layer 122 is placed atop body layer 120, and overbuild layer 124 is placed atop incisal layer 122. In some instances, it may not be necessary to place the overbuild layer on at this stage, although it is preferable. Each of these preformed layers have been previously heated, all at the same time, so as to be pliable so that they may be molded into the proper shape. The opposing dental structure 102 is then closed down upon apparatus 10 having these layers of wax layers placed thereon. Once the opposing dental structure 102 comes in contact with the pliable wax structures, each of the wax layers are molded into the proper shape and the proper custip points of opposing dental structure 102 are formed into each of the layers by arms 62. The imitation layers are then allowed to harden after upper plate 23 has been removed from contact with the layers.

Once the wax layers have hardened, a piece of adhesive material is attached to the outermost layer and the opposing dental structure 102 is again contacted with the molded wax structures. The adhesive material allows for adherence of all of the imitation wax layers to the opposing dental structure so that all of the layers are transferred to the opposing dental structure 102. Apparatus 10 is then removed from model 22 and tooth 98 is again placed in that position in model 22. As before, tooth 98 has previously been dipped in a wax substance or the like which has been allowed to harden around tooth 98. A second piece of adhesive material is placed on the upper portion of waxed-up tooth 98 and opposing dental structure 102 is again transferred into contact with tooth 98 whereby the adhesive material on tooth 98 transfers coping layer 118 onto tooth 98. Opposing dental structure 102 is again removed from contact with tooth 98 leaving only the coping wax layer 118 attached to tooth 98. The remaining wax layers remain attached to opposing dental structure 102. Now that the coping wax layer is transferred to tooth 98, the margins between the wax coping and the wax layer on tooth 98 are sealed according to methods known in the dental art. This coping is then turned into a thin metal layer by methods known in the dental art. This metal coping is then placed upon tooth 98, which no longer has a wax layer surrounding it. The metal layer forms the base structure for the porcelain crown and is in condition for placing the layers of porcelain thereon to form the finished dental crown once an opaque layer has been coated onto the metal coping.

According to the method of the present invention, each of the remaining layers of the imitation dental crown which represent the layers of porcelain to be added to the metal coping are transferred one at a time from opposing dental structure 102 onto tooth 98 which has the metal coping placed thereon. As each individual layer is transferred from opposing dental structure 102 onto tooth 98, an impression of the wax layer is obtained through use of the hinged articulator 106 as shown in FIGS. 7 and 8.

Hinged articulator 106 has a base 108, a first arm 110, and a second arm 112. On the distal end of second arm 112 a sufficient quantity of modeling clay 114 or other substance capable of making permanent impressions is attached. First arm 110 and second arm 112 are attached by means allowing second arm 112 to be pivoted about first arm 110 into a position where the modeling clay 114 contacts with and is able to cover in a manner giving a complete impression of the wax layer or layers on tooth 98. This is best shown in FIG. 8 where arm 112 and attached modeling clay 114 is shown over tooth 98, creating an impression in clay 114. The means by which arm 110 and arm 112 are coupled together can be any type of hinge, but is preferably a snap-together hinge as shown in FIG. 7. At one end of first arm 110, a notch 117 is presented which snaps tightly with a bar 116 presented on one end of second arm 112. Hinged articulator 106 is also equipped with a stop member 109 on first arm 110 and a set screw 111 on second arm 112 which allows for limiting the movement of second arm 112 onto the tooth 98. Set screw 111 can be set at different positions to accommodate different sized and positioned teeth when taking the impression of such tooth. First arm 110 further has a ball 113 at its end opposite notch 117 that is used to couple arm 110 to base 108. Base 108 has a corresponding socket 115 to receive ball 113. Ball 113 and socket 115 may be secured to a stationary position by gluing the pieces together.

Hinged articulator 106 is used when preparing porcelain crowns utilizing the various layers of preformed wax structures. Base 108 of articulator 106 is attached by any means such as glue to model 22 at a position so that it may easily obtain the impression of the wax layer on tooth 98. Once the wax coping layer 118 has been turned into metal as described above, each successive layer of wax is individually transferred onto the metal layer. Each time this is done, second arm 112 of hinged articulator 106 is pressed onto the preformed wax layer in a manner creating an impression of that particular layer in modeling clay 114. Once the impression is taken, second arm 112 is removed from hinged articulator 106 and a new arm 112 with fresh modeling clay 114 is placed thereon. The next layer of preformed wax substance is then transferred from upper dental structure 102 onto the already transferred preformed wax layers on tooth 98. An impression of the anatomy of the second preformed wax layer is then taken in the same manner as described for the first layer. This same process is repeated to obtain an impression of each of the layers in succession.

The technician preparing the porcelain crown now has at least three impressions, one corresponding to each of the body 120, incisal 122 and overbuild 124 wax layers which are required to prepare the porcelain crown.

The porcelain is prepared by standard methods known in the art and exists as a thick, semi-pourable substance. An excess quantity of porcelain is placed onto the metal coping and second arm 112 having the impression in the now hardened modeling clay that corresponds to the body layer of porcelain is placed on top of the wet porcelain. The impression in modeling clay 114 forms a mold into which the wet porcelain is shaped. Excess porcelain is removed and the porcelain within the mold corresponding to the body layer of porcelain on the crown is baked so that some of the water in the porcelain is removed. This layer will have the proper anatomical characteristics of opposing tooth 102, since the impression used as a mold corresponds to the custip points obtained through the earlier use of apparatus 10 and arms 62.

The second arm 112 having the impression of the body layer in the attached modeling clay 114 is then removed and excess porcelain is added atop the semi-dry body layer of porcelain. This amount of porcelain is formed into the correct shape by placement of second arm 112 that has the impression of the incisal wax layer in the modeling clay. Again, excess porcelain is removed and the second incisal layer of porcelain is allowed to dry and second arm 112 having the impression of the incisal layer is then removed. Finally, additional porcelain is added onto the incisal layer in order to form the overbuild layer of porcelain. Again, excess porcelain is used and the third second arm 112 having the impression of the overbuild layer in modeling clay 114 is placed thereon. Excess porcelain is removed and the porcelain overbuild layer is formed to accurately conform with the anatomical and occlusal characteristics, primarily the custip points of the opposing dental structure 102.

As a result of utilizing this method involving impressions of each of the wax layers replicating the layers of porcelain needed to be added to the metal base to create a porcelain dental crown, an anatomically accurate crown that has the proper custip points with its opposing dental structure 102 is prepared. This method removes the need for building the porcelain crown by hand and relying upon the technician's skill and experience, but rather relies on the use of molds created to accurately determine the amount of porcelain needed for each layer and the correct anatomical structure that each layer must have.

A similar method is employed to prepare replacement anterior teeth utilizing preformed wax layers corresponding to the various layers of porcelain necessary in producing such replacement dental structures. This embodiment is shown in FIG. 11. Again, a variety of sizes of preformed imitation wax layers corresponding to the body, incisal and overbuild layers necessary in preparing a porcelain anterior crown are prepared corresponding to normally sized teeth. Each of these layers are shaped like an anterior or front tooth and have predetermined thickness corresponding to the thickness of the porcelain needed to form this layer in the finished porcelain dental structure. Apparatus 10 of the present invention is not utilized in preparing anterior teeth. The anterior tooth will have been previously prepared to a base structure 126 and a replica will have been made in a stone model of the tooth as before. The first preformed wax layer 128 corresponding to the coping layer of the replacement anterior tooth is placed onto the base structure and the margins are sealed according to methods known in the dental art. This wax coping layer 128 is then turned into a metal coping that fits onto the tooth to be crowned. This metal coping forms the base of the porcelain crown. Porcelain is to be added in the proper amounts to the coping to form a crown compatible with its adjoining teeth and its opposing dental structures.

The preformed wax body layer 130 is first placed onto the metal coping and corresponds to the body layer of porcelain. Once this layer is placed on tooth 126, an impression is taken of this layer by hinged articulator 106 in a manner similar to that described above. As can be appreciated, it is only necessary to take an impression of the front portion of the tooth, as that is all that is visible when the tooth is finished and porcelain is typically only placed on this front portion. Each successive wax layer, the incisal 132 and the overbuild 134 layers, are placed on top of the previously placed layer and an individual impression is taken of each such layer using a separate second arm 112 with fresh modeling clay each time. As a result, three different impressions, each corresponding to one of the wax layers placed on the metal coping are formed in modeling clay 114 of a second arm 112. The porcelain is then prepared and added to the metal coping. A sufficient quantity of porcelain is added and the first layer 136, the body layer, of porcelain is formed by contacting the impression of the first layer in modeling clay 114 of second arm 112 onto the wet porcelain. The porcelain is allowed to dry but not to a state of complete dryness as then those next layers of porcelain could not bind to the previous layer, and this first impression removed. Some of the water in the porcelain can be removed by blotting the porcelain with tissue or the like. This results in porcelain on the metal crown in a quantity and having a shape corresponding to the proper body layer of porcelain determined to be necessary by use of the preformed, imitation wax layer. More porcelain is then added to the body layer of porcelain on the metal coping and the second impression corresponding to the incisal layer of porcelain is pressed onto the porcelain. This impression forms a mold of the correct depth and structure of the incisal layer of porcelain necessary and the excess porcelain is removed. This layer is allowed to dry and the mold is removed. Again, porcelain is added to the already existing porcelain layers and the third second arm 112 having the impression of the overbuild layer in modeling clay is placed onto the wet porcelain. This again shapes the overbuild layer properly and to the correct depth. The porcelain is allowed to dry and the mold is removed. The porcelain crown now has a metal base and three layers of porcelain thereon which is allowed to bake completely and shrink to the proper size due to the excess porcelain added in the overbuild layer. This crown is now ready for attachment to the patient's tooth.

It is also possible to utilize the above methods for preparing crowns and replacement dental structures without a metal coping layer by using a high strength porcelain that eliminates the need for the metal base.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, what is claimed is:

1. An apparatus for use in preparing dental crowns utilizing a model of a patient's dental anatomy comprising:

a base having means for defining a plurality of first linear pathways extending transversely of said base;

a plurality of upright supports having means for coupling said supports with said base and accommodating rectilinear movement of said supports over said pathway;

at least one arm extending from each of said supports and being coupled with the latter for vertical movement relative thereto;

means for holding said arm in a selected vertical position; and cap means disposed on said arms for engagement with a tooth on said model which is opposite the position of the tooth to be crowned.

2. The apparatus as set forth in claim 1 including means for defining a plurality of second linear pathways coupled with said base and extending transversely of said first linear pathways and adapted to receive said means for coupling said upright supports with said base.

3. The apparatus as set forth in claim 2 wherein said base is threaded longitudinally along said first linear pathways and said means for defining said second linear pathways is disposed above said first pathways and is also threaded longitudinally along said second pathways.

4. An apparatus for use in preparing dental crowns utilizing a model of a patient's dental anatomy comprising:

a base having means for defining a plurality of first linear pathways extending transversely of said base;

means for removably coupling said base to said model;

a plurality of upright supports having means for coupling said supports with said base and accommodating rectilinear movement of said supports over said pathway;

at least one arm extending from each of said supports and being coupled with the latter for vertical movement relative thereto; and means for holding said arm in a selected vertical position.

5. The apparatus as set forth in claim 4 wherein said first linear pathways present a plurality of slots in said base and said means for coupling each of said upright supports with said base includes:

a coupling member extending through one of said longitudinal slots and having first and second ends, said first end coupled with said upright support and said second end extending into said first linear pathway;

a hollow member coupled with said second end of said coupling member and received in said first linear pathway;

screw means having a first threaded section adapted to be threadably received in said first linear pathway and a second unthreaded section adapted to be received in said hollow member for facilitating said movement of said upright supports; and means for maintaining said screw means in relationship with said hollow member.

6. An apparatus for use in preparing dental crowns utilizing a model of a patient's dental anatomy comprising:

a base having means for defining a plurality of first linear pathways extending transversely of said base;

means defining a plurality of second linear pathways extending transversely of said first linear pathways and accommodating rectilinear movement along said second linear pathways while traversing said first linear pathways;

means for coupling said second linear pathways defining means with said first linear pathways;

a plurality of upright supports having means for coupling said supports with said second linear pathways and accommodating rectilinear movement of said supports over said second linear pathways;

at least one arm extending from each of said supports and being coupled with the latter for vertical movement relative thereto; and means for holding said arm in a selected vertical position.

7. The apparatus as set forth in claim 6 including cap means disposed on said arms for engagement with a tooth on said model which is opposite the position of the tooth to be crowned.

8. The apparatus as set forth in claim 7 wherein said first linear pathways are threaded longitudinally and said base presents longitudinally extending slots above and in communication with said first linear pathways.

9. The apparatus as set forth in claim 8 wherein said second linear pathways are threaded longitudinally and said means defining said second pathways present a longitudinally extending slot above and in communication with each of said second linear pathways.

10. The apparatus as set forth in claim 9 wherein said means for coupling said second linear pathways defining means with said first linear pathways includes:

a coupling member extending through said longitudinal slots of said base and having first and second ends, said first end coupled with said second linear pathways defining means and said second end extending into one of said first linear pathways;

a hollow member coupled with said second end of said coupling member and received in one of said first linear pathways;

screw means having a first threaded section adapted to be threadably received in said first linear pathway and a second unthreaded section adapted to be received in said hollow member for facilitating said rectilinear movement of said second linear pathways defining means within one of said first linear pathways; and means for maintaining said screw means in relationship with said hollow member.

11. The apparatus as set forth in claim 10 wherein said means for coupling said supports with said second linear pathways includes:

a coupling member extending through said longitudinal slot of said second linear pathways and having first and second ends, said first end coupled with said upright support and said second and extending into said second linear pathway;

a hollow member coupled with said second end of said coupling member and received in said second linear pathway;

screw means having a first threaded section adapted to be threadably received in said second linear pathway and a second unthreaded section adapted to be received in said hollow member for facilitating said movement of said upright supports on said second linear pathway; and means for maintaining said screw means in relationship with said hollow member.

12. The apparatus as set forth in claim 11 wherein said upright supports include first and second telescoping sections and means for holding said sections in rigid relationship whereby the height of said support is variable.

13. A method for preparing a dental crown that corresponds to the dental anatomy of its opposing dental structures and retains the same occlusal characteristics of the original dental structure utilizing a moldable, one-piece, imitation crown from which a permanent crown can be prepared, a device having a plurality of adjustable arms, and a model of a patient's dental anatomy, said model being a replica of the patient's dental structures and the corresponding occlusal characteristics of said patient's set of dental structures and where said replica of said dental structure to be crowned can be replaceably removed from said model, said method comprising the steps of:

removing said replica of said dental structure to be crowned from said model;

coating said replica of said dental structure to be crowned in a wax;

placing said device in said model where said dental structure to be crowned was located;

contacting said opposing dental structures with said device;

moving said device into occlusal contact with said opposing dental structures;

removing said opposing dental structures from contact with said device;

placing said moldable, one-piece, imitation crown onto said device;

contacting said opposing dental structures with said moldable, one-piece, imitation crown in a manner creating an impression in said moldable, one-piece, imitation crown corresponding to said occlusal characteristics of said opposing dental structures;

removing said opposing dental structures from contact with said moldable, one-piece, imitation crown;

removing said moldable, one-piece, imitation crown from said device;

removing said device from said model;

replacing said replica of said dental structure to be crowned in said model;

mounting said moldable, one-piece, imitation crown having said impression of said opposing dental structures formed thereon into said replica of said dental structure to be crowned; and forming said permanent crown from said moldable, one-piece imitation crown having said impression of said opposing dental structures formed thereon.

14. The method as set forth in claim 13 wherein said plurality of adjustable arms of said device are moved into the corresponding custip points of said opposing dental structures.

15. The method as set forth in claim 13 wherein said moldable, one-piece, imitation crown is formed from wax.

16. The method as set forth in claim 13 wherein said replica of said dental structure to be crowned is coated by dipping said replica in molten wax.

17. A preformed, imitation dental crown for use in preparing a porcelain crown having a base and a plurality of layers of porcelain thereon for a dental structure comprising:

a first preformed layer formed in a manner to surround said dental structure;

a second preformed layer formed in a manner to surround said first preformed layer and being separable from the latter;

a third preformed layer formed in a manner to surround said second preformed layer and being separable from the latter; and a fourth preformed layer formed in a manner to surround said third preformed layer and being separable from the latter, whereby said layers cooperate to form an imitation dental crown on said dental structure with separable layers corresponding to the layers of said porcelain crown, said layers being separable one at a time to accommodate stepwise buildup of the layers of porcelain which comprise said porcelain crown.

18. The preformed, imitation dental crown as set forth in claim 17 wherein said first, second, third and fourth layers are formed out of wax.

19. The preformed, imitation dental crown as set forth in claim 18 wherein said first, second, third and fourth layers are provided in a plurality of different sizes.

20. The preformed, imitation dental crown as set forth in claim 18 wherein said first, second, third and fourth layers are adapted for use on posterior teeth.

21. The preformed, imitation dental crown as set forth in claim 18 wherein said first, second, third and fourth layers adapted for use on anterior teeth.

22. A method for preparing a porcelain dental crown that corresponds to the dental anatomy of its opposing dental structures and retains the occlusal characteristics of the original dental structure utilizing a preformed, imitation dental crown having a plurality of individual preformed layers corresponding to the base structure and the individual layers of porcelain necessary to prepare said porcelain crown, a device having a plurality of adjustable arms, and a model of a patient's dental anatomy, said model being a replica of the patient's dental structures and the corresponding occlusal characteristics of said patient's set of teeth and where said replica of said dental structure to be crowned can be replaceably removed form said model, said method comprising the steps of:

removing said replica of said dental structure to be crowned from said model;

placing said device in said model where said dental structure to be crowned was located;

contacting said opposing dental structures with said device;

moving said device into occlusal contact with said opposing dental structure;

removing said opposing dental structures from contact with said device;

placing said plurality of preformed layers of said preformed, imitation dental crown onto said device;

contacting said opposing dental structures with said plurality of preformed layers in a manner creating an impression in said preformed layers corresponding to said occlusal characteristics of said opposing dental structures;

removing said preformed layers from contact with said device while maintaining said layer's contact with said opposing dental structures;

removing said device from said model;

replacing said replica of said dental structure to be crowned into said model;

transferring each individual layer of said preformed imitation dental crown to said replica;

making a mold of the characteristics of each of said individual layers of said preformed, imitation dental crown on said replica by taking an impression of said replica with said individual layer placed thereon;

utilizing said mold of each of said individual layers of said preformed, imitation dental crown to prepare said base and said layers of porcelain for said porcelain crown having said occlusal characteristics corresponding to said occlusal characteristics of said opposing dental structures.

23. A method for preparing a porcelain dental crown utilizing a preformed, imitation dental crown having a plurality of individual, preformed layers corresponding to the base structure and the individual layers of porcelain necessary to prepare said porcelain crown and a model of a patient's dental anatomy, said model being a replica of the patient's dental structures and the corresponding occlusal characteristics of said patient's set of teeth and where said replica of said dental structure to be crowned is located on said model, said method comprising the steps of:

placing each individual preformed layer of said preformed, imitation dental crown on said dental structure to be crowned;

making a mold of the characteristics of each of said individual layers of said preformed, imitation dental crown on said replica by taking an impression of said replica with said individual layer placed thereon; and utilizing said mold of each of said individual layers of said preformed, imitation dental crown to prepare said base and said layers of porcelain of said porcelain dental crown.

* * * * *

UNITED STATES PATENT AND TRADEMARK OFFICE
CERTIFICATE OF CORRECTION

PATENT NO. : 4,952,151

DATED : August 28, 1990

INVENTOR(S) : Edwin R. Metcalfe

It is certified that error appears in the above-identified patent and that said Letters Patent is hereby corrected as shown below:

In Claim 4, at column 14, line 38, delete the word "pathway" and substitute in its place -pathways-.

In Claim 10, at column 15, line 34, delete the word "slots" and substitute in its place -slot-.

In Claim 11, at colum 15, line 56, delete the word "and" (second occurrence) before the word "extending" and substitute in its place the word -end-.

In Claim 22, at column 17, line 44, delete the word "form" and substitute in its place -from-.

Signed and Sealed this

Twenty-fourth Day of December, 1991

Attest:

HARRY F. MANBECK, JR.

Attesting Officer        Commissioner of Patents and Trademarks